(12) United States Patent
Chandanson et al.

(10) Patent No.: US 10,987,138 B2
(45) Date of Patent: *Apr. 27, 2021

(54) LOCKING COMPRESSION MEMBERS FOR USE WITH BONE ANCHOR ASSEMBLIES AND METHODS

(71) Applicant: Medos International Sarl, Le Locle (CH)

(72) Inventors: Thibault Chandanson, Villers le lac (FR); Ernest Quintanilha, Norton, MA (US); Frank Spratt, Middleboro, MA (US); Philip A. Cormier, Newburyport, MA (US)

(73) Assignee: Medos International Sari, Le Locle (CH)

( * ) Notice: Subject to any disclaimer, the term of this patent is extended or adjusted under 35 U.S.C. 154(b) by 59 days.

This patent is subject to a terminal disclaimer.

(21) Appl. No.: 16/403,114

(22) Filed: May 3, 2019

(65) Prior Publication Data

US 2019/0254717 A1   Aug. 22, 2019

Related U.S. Application Data

(63) Continuation of application No. 15/643,075, filed on Jul. 6, 2017, now Pat. No. 10,321,938, which is a
(Continued)

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 17/7035* (2013.01);
(Continued)

(58) Field of Classification Search
CPC ............ A61B 17/7032; A61B 17/7035; A61B 17/7037; A61B 17/7038; A61B 17/704
See application file for complete search history.

(56) References Cited

U.S. PATENT DOCUMENTS

| 2,509,081 A | 5/1950 | Bluth et al. |
| 2,788,045 A | 4/1957 | Rosan |

(Continued)

FOREIGN PATENT DOCUMENTS

| DE | 299 03 342 U1 | 6/1999 |
| EP | 0 470 660 B1 | 7/1995 |

(Continued)

OTHER PUBLICATIONS

U.S. Appl. No. 12/365,225, filed Feb. 4, 2009, Methods for Correction of Spinal Deformities.
(Continued)

*Primary Examiner* — Jan Christopher L Merene
(74) *Attorney, Agent, or Firm* — Nutter McClennen & Fish LLP

(57) ABSTRACT

Various exemplary methods and devices are provided for fixing bone anchors to bone. In general, the methods and devices can allow for a bone anchor to be fixed to a bone at a desired angle to a surface of the bone. In an exemplary embodiment, a bone anchor assembly is provided that includes a bone anchor configured to engage bone, a receiver member for seating a head of the bone anchor, and a compression member for securing the bone anchor at fixed angle with respect to the receiver member when the compression member is seated within the receiver member. Corresponding engagement features of the compression member and the receiver member can be engaged in a secured configuration to inhibit or prevent removal of the compression cap from the receiver member and optionally to substantially prevent longitudinal and/or rotational move- (Continued)

ment of the compression member with respect to the receiver member.

13 Claims, 11 Drawing Sheets

Related U.S. Application Data continuation of application No. 14/987,812, filed on Jan. 5, 2016, now Pat. No. 9,724,130, which is a continuation of application No. 13/827,092, filed on Mar. 14, 2013, now Pat. No. 9,259,247.

(52) U.S. Cl.
CPC .............. *A61B 2017/00477* (2013.01); *A61B 2017/00526* (2013.01)

(56) References Cited

U.S. PATENT DOCUMENTS

| | | |
|---|---|---|
| 2,842,180 A | 7/1958 | Brown et al. |
| 4,124,318 A | 11/1978 | Sagady |
| 4,762,024 A | 8/1988 | Graft |
| 5,009,017 A | 4/1991 | Diekevers et al. |
| 5,102,412 A | 4/1992 | Rogozinski |
| 5,129,388 A | 7/1992 | Vignaud et al. |
| 5,154,719 A | 10/1992 | Cotrel |
| 5,281,223 A | 1/1994 | Ray |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried |
| 5,643,260 A | 7/1997 | Doherty |
| 5,672,176 A | 9/1997 | Biedermann et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B1 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,942 B2 | 5/2010 | Schumacher |
| 7,722,649 B2 | 5/2010 | Biedermann et al. |
| 7,727,261 B2 | 6/2010 | Barker et al. |
| 7,731,736 B2 | 6/2010 | Guenther et al. |
| 7,736,380 B2 | 6/2010 | Johnston et al. |
| 7,766,946 B2 | 8/2010 | Bailly |
| 7,776,072 B2 | 8/2010 | Barry |
| 7,785,354 B2 | 8/2010 | Biedermann et al. |
| 7,789,900 B2 | 9/2010 | Levy et al. |
| 7,806,914 B2 | 10/2010 | Boyd et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,172 B2 | 5/2011 | Chao et al. |
| 7,951,173 B2 | 5/2011 | Hammill, Sr. et al. |
| 7,951,175 B2 | 5/2011 | Chao et al. |
| 7,955,359 B2 | 6/2011 | Matthis et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,052,724 B2 | 11/2011 | Jackson |
| 8,057,518 B2 | 11/2011 | Frasier et al. |

(56) References Cited

U.S. PATENT DOCUMENTS

| | | |
|---|---|---|
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,308,782 B2 | 11/2012 | Jackson |
| 8,313,515 B2 | 11/2012 | Brennan et al. |
| 8,313,516 B2 | 11/2012 | Konieczynski et al. |
| 8,337,530 B2 | 12/2012 | Hestad et al. |
| 8,343,191 B2 | 1/2013 | Matthis et al. |
| 8,377,100 B2 | 2/2013 | Jackson |
| 8,409,260 B2 | 4/2013 | Biedermann et al. |
| 8,430,914 B2 | 4/2013 | Spratt et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,608,746 B2 | 12/2013 | Kolb et al. |
| 8,951,294 B2 | 2/2015 | Gennari et al. |
| 9,155,580 B2 | 10/2015 | Cormier et al. |
| 9,216,041 B2 | 12/2015 | Jackson et al. |
| 9,259,247 B2 | 2/2016 | Chandanson et al. |
| 9,402,673 B2 | 8/2016 | Cormier et al. |
| 9,433,445 B2 | 9/2016 | Ramsay et al. |
| 9,662,143 B2 | 5/2017 | Jackson |
| RE46,431 E | 6/2017 | Jackson |
| 9,700,354 B2 | 7/2017 | Jackson |
| 9,713,488 B2 | 7/2017 | Hutchinson |
| 9,724,130 B2 | 8/2017 | Chandanson et al. |
| 9,724,145 B2 | 8/2017 | Spratt et al. |
| 9,775,660 B2 | 10/2017 | Spratt et al. |
| 9,782,204 B2 | 10/2017 | Spratt et al. |
| 9,788,866 B2 | 10/2017 | Jackson |
| 9,801,665 B2 | 10/2017 | Jackson |
| 9,918,747 B2 | 3/2018 | Spratt et al. |
| 10,201,377 B2 | 2/2019 | Hutchinson |
| 10,226,282 B2 | 3/2019 | Spratt et al. |
| 10,321,938 B2 | 6/2019 | Chandanson et al. |
| 10,342,582 B2 | 7/2019 | Spratt et al. |
| 10,413,342 B2 | 9/2019 | Spratt et al. |
| 10,786,284 B2 | 9/2020 | Spratt et al. |
| 2002/0026193 A1 | 2/2002 | Barker et al. |
| 2002/0058942 A1 | 5/2002 | Biedermann et al. |
| 2002/0133159 A1 | 9/2002 | Jackson |
| 2003/0023243 A1 | 1/2003 | Biedermann et al. |
| 2003/0055426 A1 | 3/2003 | Carbone et al. |
| 2003/0073996 A1 | 4/2003 | Doubler et al. |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0153911 A1 | 8/2003 | Shluzas |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1 | 9/2005 | Biedermann et al. |
| 2005/0228326 A1 | 10/2005 | Kalfas et al. |
| 2005/0273101 A1 | 12/2005 | Schumacher |
| 2005/0277928 A1 | 12/2005 | Boschert |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0149241 A1 | 7/2006 | Richelsoph et al. |
| 2006/0161153 A1 | 7/2006 | Hawkes et al. |
| 2006/0195092 A1 | 8/2006 | Barry |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055241 A1 | 3/2007 | Matthis et al. |
| 2007/0055244 A1 | 3/2007 | Jackson |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon et al. |
| 2007/0233078 A1 | 10/2007 | Justis et al. |
| 2007/0260246 A1 | 11/2007 | Biedermann |
| 2007/0265621 A1 | 11/2007 | Matthis et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1 | 7/2008 | Nilsson |
| 2008/0172062 A1 | 7/2008 | Donahue et al. |
| 2008/0200956 A1 | 8/2008 | Beckwith et al. |
| 2008/0215100 A1 | 9/2008 | Matthis et al. |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1 | 11/2008 | Peterson et al. |
| 2008/0312692 A1 | 12/2008 | Brennan et al. |
| 2008/0319490 A1* | 12/2008 | Jackson ............. A61B 17/7022 606/308 |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0062861 A1 | 3/2009 | Frasier et al. |
| 2009/0062866 A1* | 3/2009 | Jackson ................. A61B 17/86 606/301 |
| 2009/0088803 A1 | 4/2009 | Justis et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 | 8/2009 | Hutchinson |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264896 A1 | 10/2009 | Biedermann et al. |
| 2009/0264933 A1 | 10/2009 | Carls et al. |
| 2009/0287261 A1 | 11/2009 | Jackson |
| 2009/0326587 A1 | 12/2009 | Matthis et al. |
| 2010/0004693 A1 | 1/2010 | Miller et al. |

(56) References Cited

U.S. PATENT DOCUMENTS

| | | |
|---|---|---|
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0305621 A1 | 12/2010 | Wang et al. |
| 2010/0312279 A1 | 12/2010 | Gephart et al. |
| 2011/0046683 A1 | 2/2011 | Biedermann et al. |
| 2011/0106179 A1 | 5/2011 | Prevost et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1 | 2/2012 | Jackson et al. |
| 2012/0046701 A1 | 2/2012 | Gennari et al. |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1 | 5/2012 | Biedermann et al. |
| 2012/0143266 A1 | 6/2012 | Jackson et al. |
| 2012/0150239 A1 | 6/2012 | Garamszegi |
| 2012/0165881 A1 | 6/2012 | Biedermann et al. |
| 2012/0165882 A1 | 6/2012 | Biedermann et al. |
| 2012/0179209 A1 | 7/2012 | Biedermann et al. |
| 2012/0185003 A1 | 7/2012 | Biedermann et al. |
| 2012/0197313 A1 | 8/2012 | Cowan |
| 2012/0209336 A1 | 8/2012 | Jackson et al. |
| 2012/0253404 A1 | 10/2012 | Timm et al. |
| 2012/0277805 A1 | 11/2012 | Farris |
| 2012/0303070 A1 | 11/2012 | Jackson |
| 2012/0310290 A1 | 12/2012 | Jackson |
| 2012/0316605 A1 | 12/2012 | Palagi |
| 2012/0328394 A1 | 12/2012 | Biedermann et al. |
| 2012/0330364 A1 | 12/2012 | Jacofsky et al. |
| 2013/0013003 A1 | 1/2013 | Carbone et al. |
| 2013/0046350 A1 | 2/2013 | Jackson et al. |
| 2013/0053901 A1 | 2/2013 | Cormier et al. |
| 2013/0072992 A1* | 3/2013 | Jackson ............. A61B 17/7005 606/305 |
| 2013/0096618 A1 | 4/2013 | Chandanson et al. |
| 2013/0096623 A1 | 4/2013 | Biedermann et al. |
| 2013/0103093 A1 | 4/2013 | Biedermann et al. |
| 2013/0110172 A1 | 5/2013 | Biedermann et al. |
| 2013/0110180 A1 | 5/2013 | Doubler et al. |
| 2013/0144346 A1 | 6/2013 | Jackson et al. |
| 2013/0150904 A1 | 6/2013 | Biedermann et al. |
| 2013/0211467 A1 | 8/2013 | Dickinson |
| 2014/0018861 A1 | 1/2014 | Hutchinson |
| 2014/0025119 A1 | 1/2014 | Biedermann et al. |
| 2014/0094849 A1 | 4/2014 | Spratt et al. |
| 2014/0142633 A1 | 5/2014 | Jackson et al. |
| 2014/0142634 A1 | 5/2014 | Schlaepfer et al. |
| 2014/0214097 A1* | 7/2014 | Jackson ............. A61B 17/7091 606/305 |
| 2014/0277153 A1 | 9/2014 | Spratt et al. |
| 2014/0277157 A1 | 9/2014 | Chandanson et al. |
| 2014/0277158 A1 | 9/2014 | Spratt et al. |
| 2014/0277159 A1 | 9/2014 | Spratt et al. |
| 2014/0277161 A1 | 9/2014 | Spratt et al. |
| 2014/0277162 A1 | 9/2014 | Kostuik et al. |
| 2014/0277189 A1 | 9/2014 | Spratt et al. |
| 2015/0173816 A1 | 6/2015 | Biedermann et al. |
| 2016/0128733 A1 | 5/2016 | Spratt et al. |
| 2016/0135848 A1 | 5/2016 | Chandanson et al. |
| 2017/0296235 A1 | 10/2017 | Chandanson et al. |
| 2017/0354446 A1 | 12/2017 | Spratt et al. |
| 2017/0354448 A1 | 12/2017 | Hutchinson |
| 2017/0360482 A1 | 12/2017 | Spratt et al. |
| 2017/0360491 A1 | 12/2017 | Spratt et al. |
| 2019/0239936 A1 | 8/2019 | Hutchinson |
| 2019/0365426 A1 | 12/2019 | Spratt et al. |

FOREIGN PATENT DOCUMENTS

| | | |
|---|---|---|
| EP | 1 295 566 A1 | 3/2003 |
| EP | 0 857 465 B1 | 6/2003 |
| EP | 1 570 794 A1 | 9/2005 |
| EP | 1 774 919 B1 | 8/2008 |
| EP | 1 795 134 B1 | 8/2008 |
| EP | 2 070 485 A1 | 6/2009 |
| EP | 1 694 229 B1 | 7/2010 |
| EP | 2 272 451 A1 | 1/2011 |
| EP | 2 286 748 A1 | 2/2011 |
| EP | 2 455 028 A1 | 5/2012 |
| EP | 2 129 310 B1 | 9/2012 |
| WO | 91/016020 A1 | 10/1991 |
| WO | 2004/058081 A1 | 7/2004 |
| WO | 2008/024937 A2 | 2/2008 |
| WO | 2008/119006 A1 | 10/2008 |
| WO | 2009/073655 A1 | 6/2009 |
| WO | 2010/056846 A2 | 5/2010 |
| WO | 2011/059732 A1 | 5/2011 |
| WO | 2011/109009 A1 | 9/2011 |
| WO | 2011/127065 A1 | 10/2011 |
| WO | 2012/024665 A2 | 2/2012 |
| WO | 2012/030712 A1 | 3/2012 |
| WO | 2012/035479 A2 | 3/2012 |
| WO | 2012/060868 A1 | 5/2012 |
| WO | 2013/028851 A1 | 2/2013 |

OTHER PUBLICATIONS

U.S. Appl. No. 13/205,248, filed Aug. 8, 2011, Methods for Correction of Spinal Deformities.
U.S. Appl. No. 13/804,012, filed Mar. 14, 2013, Bone Anchors and Surgical Instruments With Integrated Guide Tips.
U.S. Appl. No. 13/826,161, filed Mar. 14, 2013, Bone Anchor Assemblies and Methods With Improved Locking.
U.S. Appl. No. 13/827,092, filed Mar. 14, 2013, Locking Compression Members for Use With Bone Anchor Assemblies and Methods.
U.S. Appl. No. 13/828,236, filed Mar. 14, 2013, Bone Anchor Assemblies With Multiple Component Bottom Loading Bone Anchors.
U.S. Appl. No. 13/828,882, filed Mar. 14, 2013, Bottom-Loading Bone Anchor Assemblies and Methods.
U.S. Appl. No. 13/829,000, filed Mar. 14, 2013, Bottom-Loading Bone Anchor Assemblies.
U.S. Appl. No. 14/029,005, filed Sep. 17, 2013, Bone Anchor Assemblies.
U.S. Appl. No. 14/029,037, filed Sep. 17, 2013, Methods for Correction of Spinal Deformities.
U.S. Appl. No. 14/070,943, filed Nov. 4, 2013, Bone Anchor Assemblies and Methods With Improved Locking.
U.S. Appl. No. 14/966,531, filed Dec. 11, 2015, Bone Anchor Assemblies and Methods With Improved Locking.
U.S. Appl. No. 14/987,812, filed Jan. 5, 2016, Locking Compression Members for Use With Bone Anchor Assemblies and Methods.
U.S. Appl. No. 15/629,825, filed Jun. 22, 2017, Methods for Correction of Spinal Deformities.

(56) References Cited

OTHER PUBLICATIONS

U.S. Appl. No. 15/634,630 filed Jun. 27, 2017, Bone Anchor Assemblies With Multiple Component Bottom Loading Bone Anchors.
U.S. Appl. No. 15/643,075, filed Jul. 6, 2017, Locking Compression Members for Use With Bone Anchor Assemblies and Methods.
U.S. Appl. No. 15/692,166, filed Aug. 31, 2017, Bone Anchor Assemblies.
U.S. App. No. 15/692,822, filed Aug. 31, 2017, Bottom-Loading Bone Anchor Assemblies and Methods.
U.S. Appl. No. 16/277,889, filed Feb. 15, 2019, Bone Anchor Assemblies.
U.S. Appl. No. 61/706,860, filed Sep. 28, 2012, Devices and Methods for Breaking and Retaining Surgical Reduction Tabs.
U.S. Appl. No. 61/707,062, filed Sep. 28, 2012, Bone Anchor Assemblies.
U.S. Appl. No. 16/271,607, filed Feb. 8, 2019, Methods for Correction of Spinal Deformities.
[No Author Listed] A New Angle on Correction. Expedium. DePuy. 2009. 2 pages.
[No Author Listed] Definition of "clip," www.thefreedictionary.com/clip; accessed May 16, 2015.
[No Author Listed] Moss Miami Polyaxial Reduction Screw Surgical Technique, DePuy AcroMed, Inc. 1998.
[No Author Listed] Straight Talk with Expedium. Expedium. 10 pages. Jul. 2007.
[No Author Listed] Surgical Technique Guide and Ordering Information. Expedium. DePuy Spine Inc. Sep. 2011. 24 Pages.
[No Author Listed] Value Analysis Brief—Expedium Favored Angle Screw. DePuy Synthes Spine. Aug. 2012. 4 pages.
[No Author Listed] Viper 2 MIS Extended Tab , DePuy Spine, Inc., Feb. 1, 2009.
Duerig, T. W., et al., "An Engineer's Perspective of Pseudoelasticity," p. 370, in Engineering Aspects of Shape Memory Alloys, Butterworth-Heinemann, 1990.
International Search Report and Written Opinion for Application No. PCT/US2013/060350, dated Jan. 3, 2014 (9 pages).
International Search Report for PCT/US14/021198 dated Jun. 5, 2014 (3 Pages).
International Preliminary Report on Patentability for Application No. PCT/US2014/021198, dated Sep. 24, 2015 (7 pages).
[No Author Listed] Expedium Spine System, Dual Innie Independent Locking Technology Brochure, DePuy Spine, Aug. 1, 2004, 6 pages.
[No Author Listed] Viper 2 MIS Spine System, System Guide. DePuy Spine Inc. Sep. 2011. 60 pages.
U.S. Appl. No. 61/706,860, filed Sep. 28, 2012 (66 pages).

\* cited by examiner

LOCKING COMPRESSION MEMBERS FOR USE WITH BONE ANCHOR ASSEMBLIES AND METHODS

CROSS-REFERENCE TO RELATED APPLICATIONS

This application is a continuation of U.S. patent application Ser. No. 15/643,075 filed on Jul. 6, 2017. U.S. patent application Ser. No. 15/643,075 is a continuation of U.S. patent application Ser. No. 14/987,812 filed on Jan. 5, 2016. U.S. patent application Ser. No. 14/987,812 is a continuation of U.S. patent application Ser. No. 13/827,092 filed on Mar. 14, 2013. The entire contents of each of these applications is incorporated by reference herein.

FIELD

The present invention relates to methods and devices for correcting a spine, and in particular to bone anchor assemblies and methods of using the same.

BACKGROUND

Bone anchors may be used in orthopedic surgery to fix bone during healing or during a fusion process. In spinal surgery, bone anchors may be used with spinal fixation elements, such as spinal rods, to stabilize multiple vertebrae either rigidly, in which no relative motion between the vertebrae is desired, or dynamically, in which limited, controlled motion between the vertebrae is desired. Fixation elements can help to support the spine in a desired alignment, for example by defining a shape towards which a deformed spine is to be corrected. Attaching the vertebrae to the fixation element causes vertebrae which are out of position to be drawn towards the fixation element, so that they can then be retained in a correct alignment against forces imposed by soft tissue tending to revert the configuration of the spine towards the deformed shape. Correction of the spinal deformation can involve application to the vertebrae of translational forces, torsional forces, or combinations thereof to cause vertebrae to translate and/or rotate.

Surgical procedures using bone anchors often require that the bone anchor be secured to the bone at a predetermined angle to a surface of the bone. Traditional bone anchors can include a shaft having a spherical head that is polyaxially seated in a receiver member and that can be secured at a fixed angle to the receiver member by a compression member. To reduce a risk that the compression member is misplaced or dropped into a surgical incision in a patient before the compression member is secured proximally of the head, traditional methods can require deformation of the receiver member against the compression cap. The deformation process, called "swaging," compresses the receiver member against the compression cap to substantially prevent relative movement therebetween. However, the swaging process can weaken the structure of the bone anchor and can increase the expense and the time required for manufacturing of the bone anchor.

Accordingly, there remains a need for improved methods and devices for bone anchor fixation.

SUMMARY

The present invention generally provides methods and devices for fixing a bone anchor to a bone. In one aspect, a bone screw assembly is provided that can include a screw having a proximal portion and a distal shank portion, a receiver member having a polyaxial seat formed therein and configured to proximally seat the head portion of the screw, and a compression cap. The compression cap can be disposed within the receiver member and can have a distal end configured to engage the head portion of the screw. Opposed projections of the compression cap can extend radially therefrom and can be configured to mate with complementary recesses formed in the receiver member such that the compression cap is retained within the receiver member.

The opposed projections can be configured in any number of ways. A distance between outer surfaces of the opposed projections can be greater than the inside diameter of the receiver member, although the compression cap can have an outside diameter that is less than an inside diameter of the receiver member. A width of each projection measured horizontally about the circumference of the compression cap can be greater than a thickness of the opposed projection measured along a radial axis of the compression cap. The opposed projections can be configured such that movement of the compression cap distally within the receiver member is effective to deform the opposed projections until the opposed projections snap into engagement with the complementary recesses. Rotating the compression cap relative to the receiver member can also be effective to deform the opposed projections until the opposed projections snap into engagement with the complementary recesses, and/or can be effective to move the opposed projections into engagement with the complementary recesses. The opposed projections and the complementary recesses can be effective, when mated, to maintain the compression cap in a substantially fixed longitudinal and/or rotational position relative to the receiver member.

A proximal-facing surface of each projection and an inner superior surface of each complementary recess can be planar such that, when mated, the compression cap is prevented from being decoupled from the receiver member. A distal-facing surface of each projection can be ramped, tapered, chamfered, and/or beveled to provide a lead-in surface geometry. Similarly, the receiver member can include a shoulder disposed proximal to the complementary recesses, the shoulder being ramped, tapered, chamfered, and/or beveled to provide a lead-in surface for the opposed projections as the compression cap is advanced distally relative to the receiver member. Where the complementary recesses comprise cut-outs formed in a shelf that extends radially inward from an interior sidewall of the receiver member, the shelf can include one or more lateral edges that are ramped, tapered, chamfered, and/or beveled to provide a lead-in surface for the opposed projections.

In another aspect, a method is provided for assembling a bone screw that can include passing a shank portion of the bone screw through an aperture formed in a distal end of a receiver member, inserting a compression cap into the receiver member, and engaging opposed projections extending radially outward from the compression cap with complementary recesses formed in the receiver member to retain the compression cap within the receiver member. The method can further include deforming the projections over a shoulder portion of the receiver member disposed proximal to the complementary recesses. The engaging can be effective to maintain the compression cap in a substantially fixed longitudinal and/or rotational position relative to the receiver member. Inserting the compression cap can comprise sliding the compression cap distally within the receiver member to deform the opposed projections until the opposed rejections snap into engagement with the complementary recesses. Inserting the compression cap can also comprise rotating the compression cap relative to the receiver member to move the opposed projections into engagement with the complementary recesses. Where the complementary recesses can be formed in a shelf that extends radially inward from an interior sidewall of the receiver member, the engaging can comprise camming the opposed projections over ramped, tapered, chamfered, and/or beveled edges of the shelf and snapping the opposed projections into the complementary recesses.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
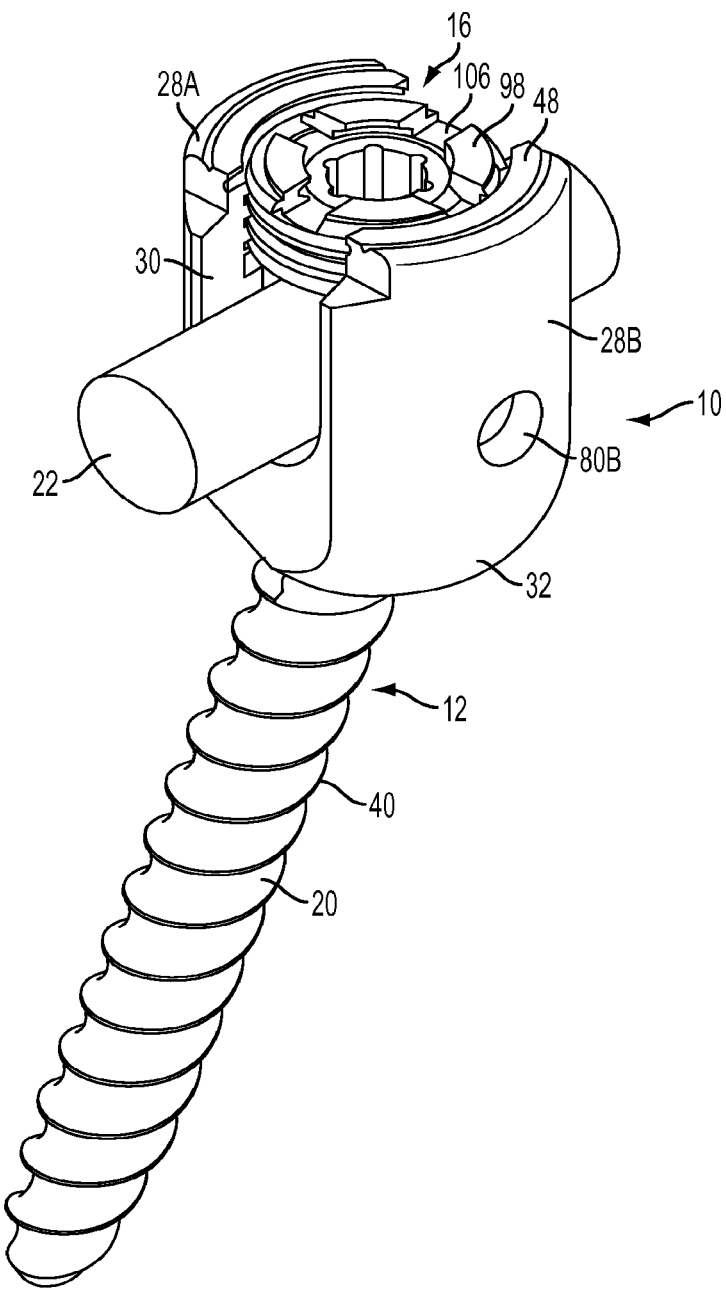
FIG. 1A (PRIOR ART) is a perspective view of a prior art bone anchor assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for fixing bone anchors to bone. In general, the methods and devices can allow for a bone anchor to be fixed to a bone at a desired angle relative to a receiver member. In an exemplary embodiment, a bone anchor assembly is provided that includes a bone anchor configured to engage bone, a receiver member for seating a head of the bone anchor, and a compression member for securing the receiver member at fixed angle with respect to the bone anchor. The compression member can be seated within the receiver member, proximally of the head of the bone anchor, and can include one or more engagement features to facilitate attachment to the receiver member. Similarly, the receiver member can include one or more complementary engagement features that correspond to the engagement features of the compression member. Mating between the corresponding engagement features of the compression member and the receiver member in a secured configuration can be sufficient to inhibit or prevent removal of the compression member from the receiver member, thus reducing a risk of accidental loss or misplacement of the compression member. Engagement of the corresponding engagement features can optionally be sufficient to substantially prevent longitudinal and/or rotational movement of the compression member with respect to the receiver member, such that once the compression member is in the secured configuration, the compression member can exert a distal force on the head of the bone anchor and can substantially fix the bone anchor at the desired angle with respect to the receiver member.

FIGS. 1A-1D illustrate a prior art bone anchor assembly 10 that includes a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 and the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Publication No. 2013/0053901, filed Aug. 25, 2011, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly 10, including, for example, the closure mechanism 16, the receiver member 14, and the compression member 60 (discussed below) can be cannulated or otherwise have an opening to permit delivery over a guide wire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyl apatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The arms 28A, 28B can include a feature, such as a bore, recess, dimple, notch, projection, or the like, to facilitate connection of the receiver member 14 to instruments. In the exemplary embodiment, opposing bores 80A, 80B are formed on the arms 28A, 28B for insertion of two pins as part of a swaging process, described in more detail below. The outer surface of each arm 28A, 28B can further include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 14 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 12. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12. A largest diameter of the compression member 60 can be smaller than a smallest inner diameter of the receiver member 14 to allow the compression member 60 to fit within the recess 30 of the receiver member 14.

Figure 1B:
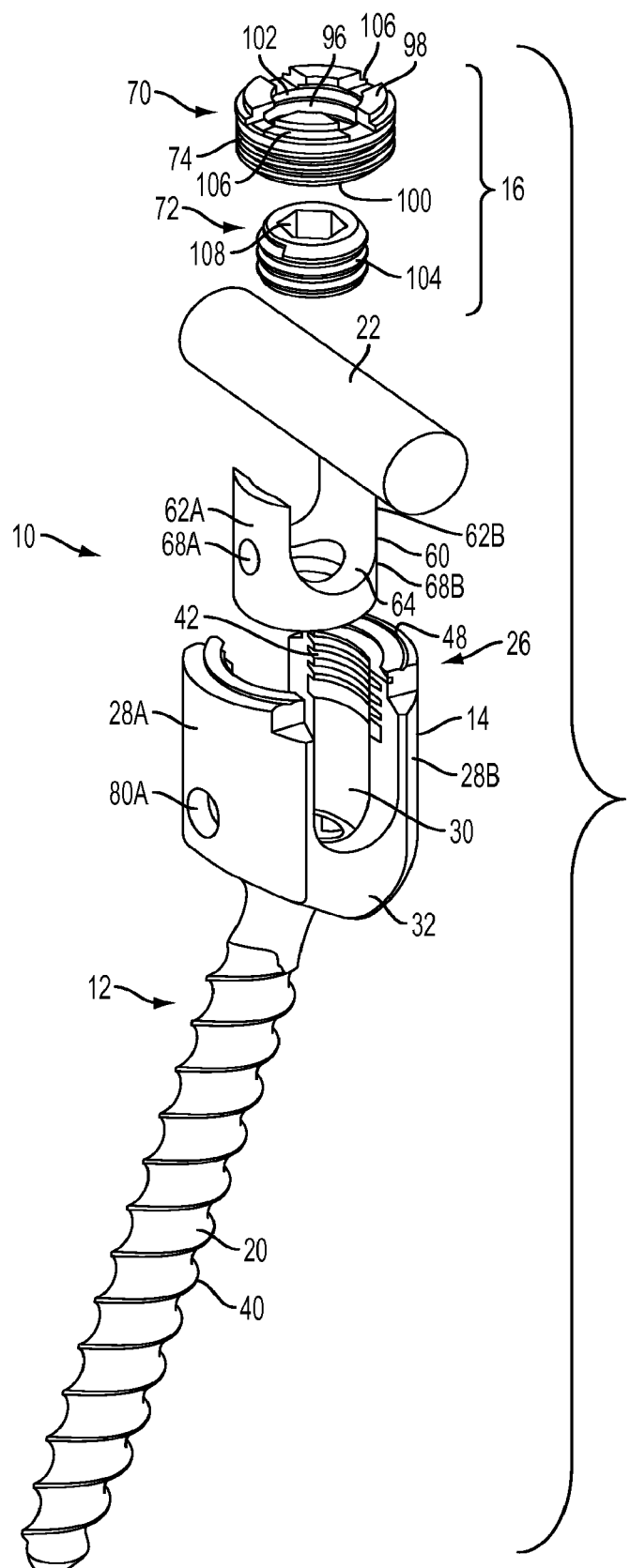
FIG. 1B (PRIOR ART) is an exploded view of the bone anchor assembly of FIG. 1A.
Figure 1C:
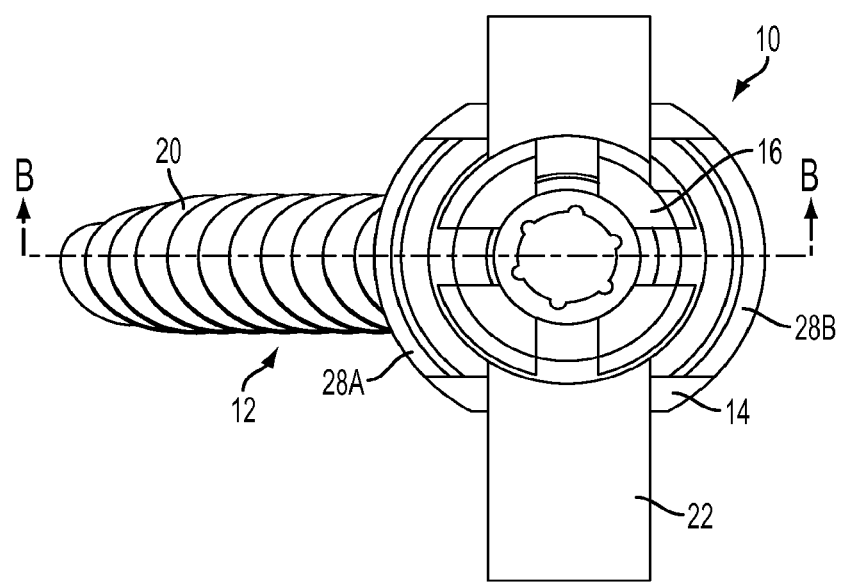
FIG. 1C (PRIOR ART) is a top view of the bone anchor assembly of FIG. 1A.
Figure 1D:
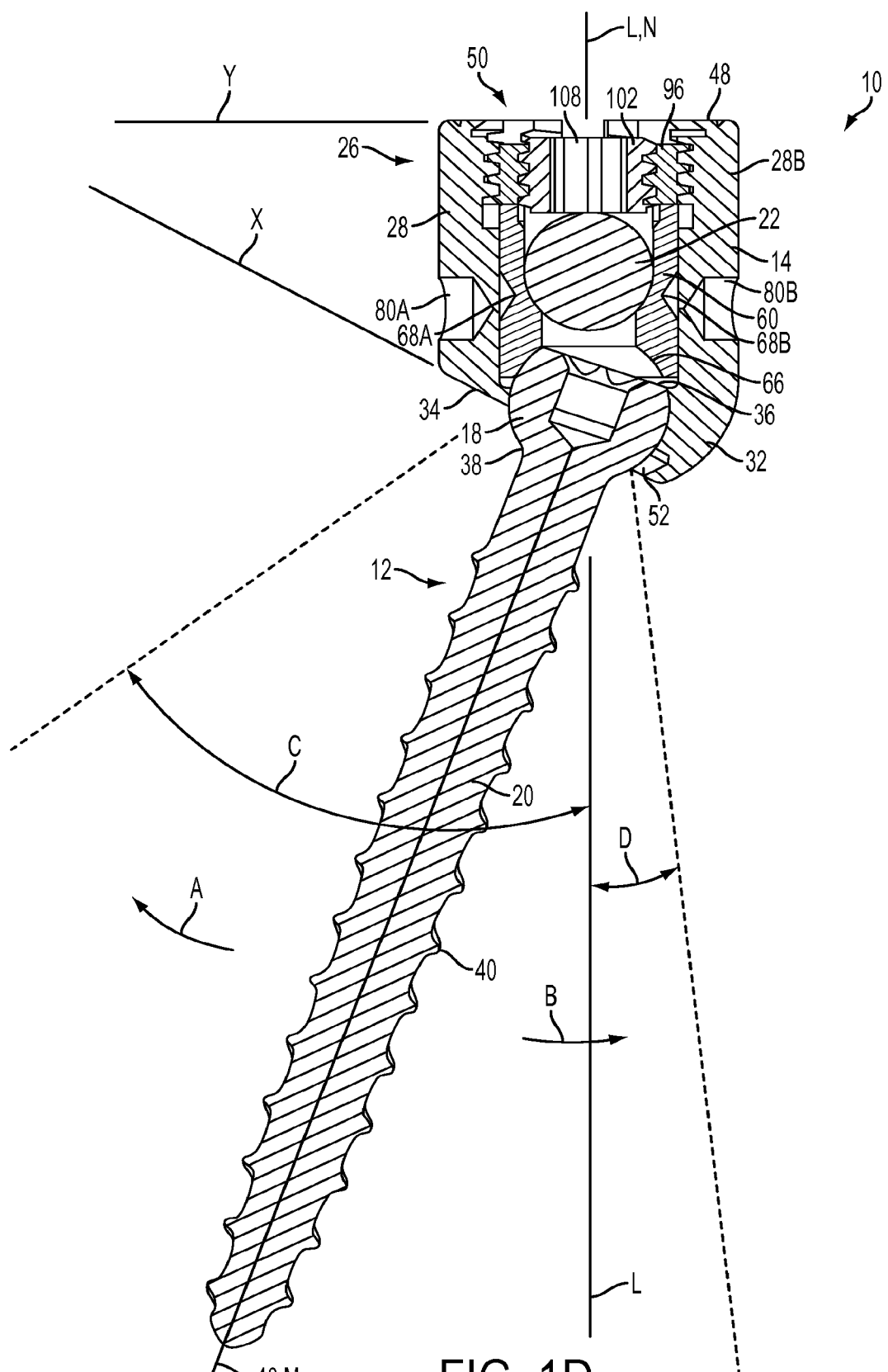
FIG. 1D (PRIOR ART) is a cross-sectional view of the bone anchor assembly of FIG. 1A.

As best seen in FIG. 1B, the compression member 60 is configured to slide freely along the longitudinal axis L within the slot 30 of the receiver member 14. To secure the compression cap 60 in place within the receiver member 14, the compression member 60 is configured to be mechanically deformed against the receiver member 14. Opposing bores 68A, 68B formed on the arms 62A, 62B of the compression member 60 are aligned with the bores 80A, 80B of the receiver member 14, such that opposing pins can be inserted through the passageways defined by bores 68A, 80A and bores 68B, 80B to compress or "swage" the compression member 60 against the receiver member 14. The swaging process can prevent subsequent removal of the compression member 60 from the receiver member 14.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can includes an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 72 can include drive features for receiving an instrument to rotate and advance the inner set screw 72 relative to the outer set screw 74. The illustrated inner set screw 72 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae.

In use, bone can be prepared to receive the bone anchor assembly 10, generally by drilling a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into the prepared hole in the bone. The compression member 60 can be positioned within the receiver member 14 such that the arms 62A, 62B of the compression member are aligned with the arms 28A, 28B of the receiver member 14 and the distal surface 66 of the compression member 60 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14.

One or more embodiments of inventive bone anchor assemblies are described below. Except as indicated below, the structure, operation, and use of these embodiments is similar or identical to that of the bone anchor assembly 10 described above. Accordingly, a detailed description of said structure, operation, and use is omitted here for the sake of brevity.

FIGS. 2-6 illustrate an exemplary embodiment of a bone anchor assembly 110 that includes a compression cap 160 configured to mate to and engage a receiver member 114 such that the compression cap 160 is retained within the receiver member 114. The compression cap 160 is configured to be seated within a recess 130 of the receiver member 114, proximally of the bone anchor 112, and the compression cap 160 can include features formed thereon that engage corresponding engagement features formed on the receiver member 114. Once mated to the receiver member 114, the compression cap 160 can apply a frictional force to the bone anchor 112 to substantially maintain the anchor 112 at a desired angle with respect to the receiver member 114, while still allowing the angular orientation of the anchor 112 to be adjusted. Engagement of the corresponding engagement features can be sufficient to prevent removal of the compression cap 160 from the receiver member 114, and optionally to substantially prevent longitudinal and/or rotational movement of the compression cap 160 with respect to the receiver member 114 when no force is applied thereto.

Engagement features of the compression cap 160 for engaging the receiver member 114 can be formed anywhere on a surface of the compression cap 160 that is configured to contact the receiver member 114. In the illustrated embodiment, the engagement features are in the form of wings 161A, 161B that project radially outward from outward-facing surfaces of the opposed arms 162A, 162B, distally of flanges 165A, 165B on the arms 162A, 162B. The wings 161A, 161B can extend around an entire width of each of the arms 162A, 162B measured along a circumference of the compression cap 160, although it will be appreciated that the width We of the wings 161A, 161B can be smaller than the width of the arms 162A, 162B, and can be either the same or different from one another. Moreover, it will be appreciated that although the illustrated wings 161A, 161B extend in a plane that is substantially perpendicular to the longitudinal axis $L_1$ of the compression cap 160, the wings 161A, 161B can extend in any plane, either the same or different from one another.

Figure 2:
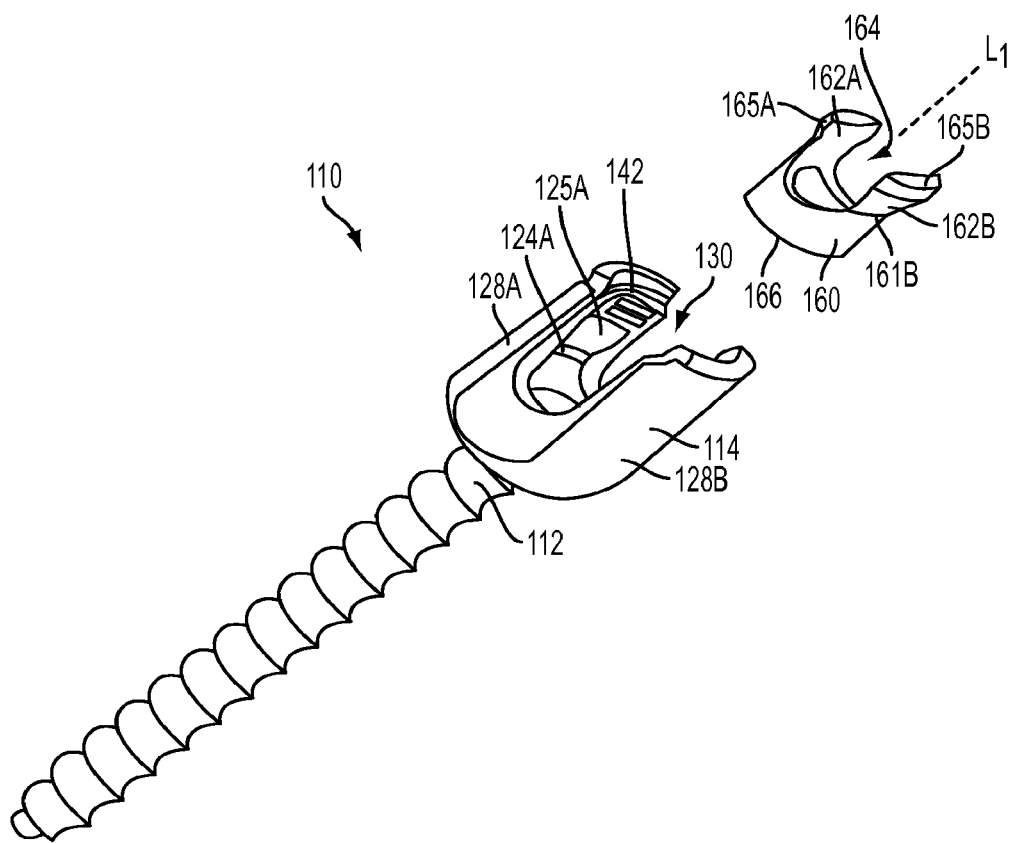
FIG. 2 is a perspective, partially exploded view of a bone anchor assembly including a bone anchor, a receiver member, and a compression cap.
Figure 3:
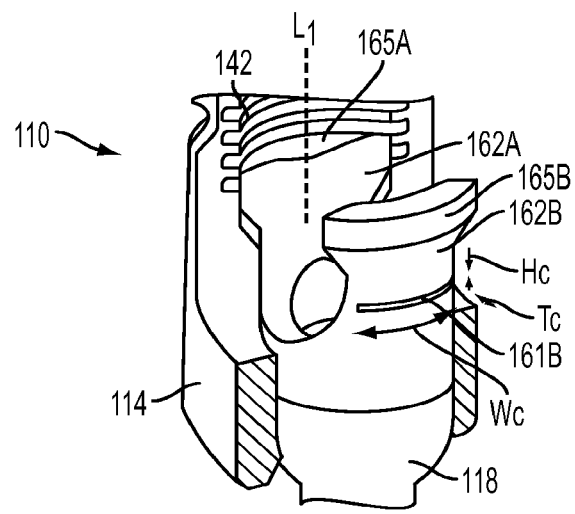
FIG. 3 is a perspective, partial cut-away view of the bone anchor assembly of FIG. 2.
Figure 4:
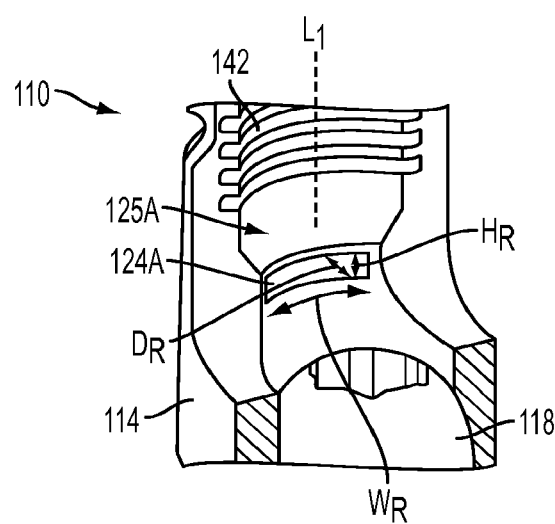
FIG. 4 is a cut-away view of the receiver member and the bone anchor of the bone anchor assembly of FIG. 2.

The longitudinal position of the wings 161A, 161B along the longitudinal length of the compression cap 160 can vary, but preferably the wings 161A, 161B are formed at a location that corresponds to a location of complementary engagement features in the receiver member 114, discussed below, and at a location that will retain the compression cap 160 within the receiver member 114 at a predetermined position just proximal to the head of the bone anchor 112, and more preferably at a predetermined position effective to apply some amount of frictional force to the head of the bone anchor 112. As shown in FIG. 2, the wings 161A, 161B are located distal to the flanges 165A, 165B and proximal to the distal end 166 and also just proximal to the distal-most end of the U-shaped cut-out 164 formed in the compression cap 160.

The wings 161A, 161B can have any shape and dimension, either the same or different from one another. In the illustrated embodiment, the wings 161A, 161B are in the form of elongate protrusions or ridges formed on the outer surface of each arm 162A, 162B. The wings 161A, 161B have a width We measured horizontally about a circumference of the compression cap 160, a height He measured along a longitudinal axis $L_1$ of the compression cap 160, and a depth or thickness $T_C$ measured along a radial axis of the compression cap 160. The width We of the wings 161A, 161B can vary depending on the total width of the arms 162A, 162B, and the width We can be equal to or less than a total width of the arms 162A, 162B. The height He and thickness $T_C$ of the wings 161A, 161B can also vary, but preferably the height He and thickness $T_C$ are small enough to allow for insertion of the compression cap 160 into the recess 130 of the receiver member 114. In some embodiments, the wings 161A, 161B have a height He and thickness $T_C$ that are small enough to allow the wings 161A, 161B to deflect as the compression cap 160 is inserted into the receiver member 114, as described in more detail below. Although the engagement features of the illustrated embodiment are in the form of wings 161A, 161B, it will be appreciated by a person skilled in the art that the compression cap 160 can have a variety of engagement features thereon for engaging the receiver member 114. Moreover, although there are only two wings 161A, 161B in the illustrated embodiment, it will be appreciated by a person skilled in the art that the compression cap 160 can have any number of engagement features formed thereon.

One or more complementary engagement features can be formed on the receiver member 114. In the illustrated embodiment, best shown in FIG. 4, the receiver member 114 includes pockets 124A, 124B formed on inner walls of the opposed arms 128A, 128B. The pockets 124A, 124B are configured to seat the wings 161A, 161B of the compression cap 160 when the compression cap 160 is in a secured configuration. The location of the pockets 124A, 124B within the receiver member 114 can vary, but as indicated above with respect to the compression cap 160, the pockets 124A, 124B are preferably at a location that seats the compression cap 160 in a predetermined position that is proximal of the head of the bone anchor 112. The location can also be configured to position the u-shaped cut-outs formed between the arms 162A, 162B of the compression cap 160 in alignment with u-shaped cut-outs formed between the arms 128A, 128B of the receiver member 114. In the illustrated embodiment, the pockets 124A, 124B are located distal of the threads 142 formed in a proximal portion of the receiver member 114, and proximal of the distal-most end of the u-shaped cut-outs formed between the arms 128A, 128B.

The pockets 124A, 124B can have any shape and dimension, either the same or different from one another, but they preferably have a shape and size that allows the wings 161A, 161B to be seated and retained therein. At least one dimension of the pockets 124A, 124B can be substantially the same as or slightly smaller than a corresponding dimension of the wings 161A, 161B to provide for an interference fit between the wings 161A, 161B and the pockets 124A, 124B, and/or at least one dimension of the pockets 124A, 124B can be slightly larger than a corresponding dimension of the wings 161A, 161B to allow for some adjustment of the compression cap 160 within the recess 130 when the compression cap 160 is in the secured configuration. In an exemplary embodiment, the pockets 124A, 124B have a width $W_R$ measured horizontally about a circumference of the receiver member 114 that is substantially the same as the width We of the wings 161A, 161B, a depth $D_R$ measured along a radial axis of the receiver member 114 that is substantially the same as the thickness $T_C$ of the wings 161A, 161B, and a height $L_R$ measured along the longitudinal axis $L_1$ of the compression cap 160 that is substantially the same as a height He of the wings 161A, 161B. A total diameter between an outer-most surface of each of the wings 161A, 161B can also be greater than an inner diameter of the receiver member 114 so as to prevent removal of the compression cap 160 once mated with the receiver member 114. A tight fit between at least two of the corresponding dimensions, e.g., between the width We of the compression cap 160 and the width $W_R$ of the receiver member 114, and/or between the height He of the compression cap 160 and the height $H_R$ of the receiver member 114, and/or between the thickness $T_C$ of the compression cap 160 and the depth $D_R$ of the receiver member 114, can help to substantially prevent both longitudinal and rotational movement of the compression cap 160 once the compression cap 160 is in the secured configuration. A small difference between the height He of the wings 161A, 161B and the height $H_R$ of the pockets 124A, 124B can allow for proximal-distal movement of the compression cap 160, thus allowing for further tightening of the compression cap 160 against the bone anchor 112. This can be achieved by applying a closure member (not shown) to the receiver member 114 so as to cause a spinal fixation rod seated within the receiver member 114 to apply a distal force to the compression cap 160 to thereby cause the compression cap 160 to frictionally engage and lock the bone anchor 112 in a fixed position relative to the receiver member 114. In addition, as will be explained in more detail below, the additional space within the pockets 124A, 124B along the longitudinal axis $L_1$ of the compression cap 160 can allow for the bone anchor 112 to assume various angles with respect to the longitudinal axis $L_1$ of the compression cap 160 prior to locking the bone anchor assembly. In an exemplary embodiment, the relative heights $H_C$, $H_R$ are configured so as to cause the compression cap 160 to apply friction to the bone anchor 112 to maintain the bone anchor 112 at a desired angle when no closure mechanism is applied to the receiver member 114. The friction can be overcome by applying a force to the receiver member 114 to adjust the angle as desired.

As indicated above, the corresponding engagement features of the compression cap 160 and the receiver member 114 can be configured to facilitate insertion of the compression cap 160 into the receiver member 114, but to inhibit or prevent removal of the compression cap 160 from the receiver member 114. As the compression cap 160 is distally advanced from an unsecured configuration, shown in FIG. 5, where the wings 161A, 161B are proximal of and not seated within the pockets 124A, 124B, toward a secured configuration, shown in FIG. 6, where the wings 161A, 161B are seated within the pockets 124A, 124B, a user can apply a distally-directed force to overcome the resistive force of the wings 161A, 161B against the inner walls of the receiver member 114. The resistive force can be reduced by complementary lead-in surface geometries of the wings 161A, 161B and the receiver member 114. In the illustrated embodiment, the wings 161A, 161B have ramped distal-facing surfaces that are complementary to ramped shoulders 125A, 125B of the arms 128A, 128B of the receiver member 114, such that the wings 161A, 161B can slide along the shoulders 125A, 125B of the arms 128A, 128B as the compression cap 160 is advanced distally into the recess 130.

To further facilitate insertion of the compression cap 160 into the receiver member 114, one or all of the wings 161A, 161B, the cap's arms 162A, 162B, and the receiver's arms 128A, 128B can be formed from one or more flexible materials. In one embodiment, the wings 161A, 161B can be formed from one or more flexible materials that can allow the wings 161A, 161B to deflect or bend proximally as the wings 161A, 161B pass through the receiver member 114 and into the pockets 124A, 124B. In another embodiment, the wings 161A, 161B can be formed from a shape memory material that can allow the wings 161A, 161B to compress or deform inwardly as the wings 161A, 161B pass through the receiver member 114 and then expand once the wings 161A, 161B are seated within the pockets 124A, 124B. In another embodiment (not shown), the wings 161A, 161B can be biased inwardly, e.g., by springs, and can deflect outwardly as the compression cap 160 is advanced through the receiver member 114 and then return to the biased inward position once the wrings 161A, 161B are aligned with the pockets 124A, 124B. As the wings 161A, 161B pass into the pockets 124A, 124B, the wings 161A, 161B can snap into engagement with the pockets 124A, 124B, thus providing tactile feedback to a user and helping to inhibit or prevent subsequent removal of the compression cap 160 from the receiver member 114. Similarly, the arms 162A, 162B of the compression cap 160 can deflect inwardly as the compression cap 160 is inserted into the recess 130, and/or the arms 128A, 128B of the receiver member 114 can deflect outwardly as the compression cap 160 is inserted into the recess 130.

To inhibit or prevent removal of the compression cap 160 from the receiver member 114, the wings 161A, 161B can have proximal-facing surfaces that extend in a plane substantially perpendicular to the longitudinal axis $L_1$ of the compression cap 160. Once the wings 161A, 161B are seated within the pockets 124A, 124B in the secured configuration, the proximal-facing surfaces of the wings 161A, 161B can abut distal-facing surfaces of the pockets 124A, 124B, which can also extend in a plane substantially perpendicular to the longitudinal axis $L_1$ of the compression cap 160. In addition, the wings 161A, 161B can be configured such that distal or outward flexion of the wings 161A, 161B away from the compression cap 160 is more difficult to achieve than any proximal or inward flexion of the wings 161A, 161B toward the compression cap 160 that is required for insertion of the wings 161A, 161B into the pockets 124A, 124B, e.g., the wings 161A, 161B can be biased proximally.

Figure 5A:
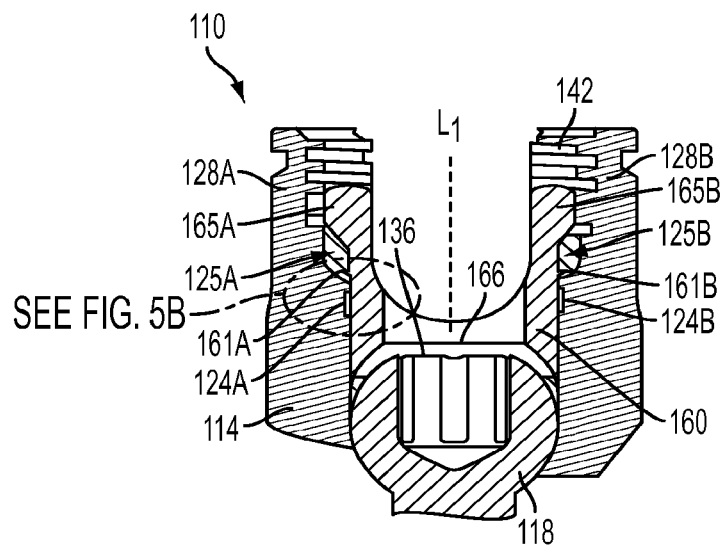
FIG. 5A is a partial cross-sectional view of the bone anchor assembly of FIG. 2 before the compression cap has been attached to the receiver member.
Figure 5B:
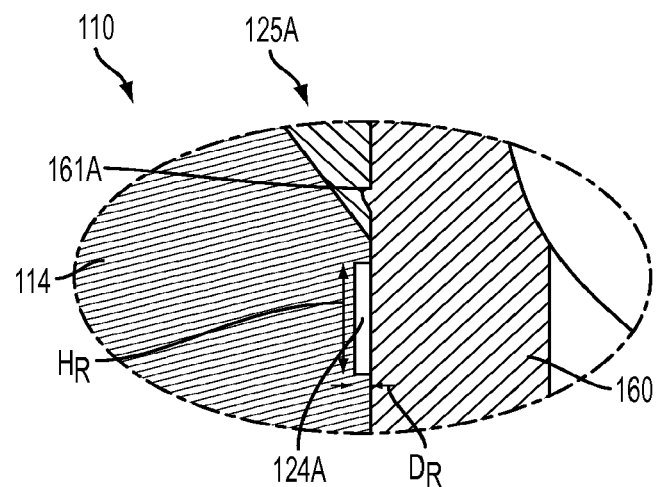
FIG. 5B is an enlarged cross-sectional view of the compression cap and the receiver member of the bone anchor assembly of FIG. 2 before the compression cap has been attached to the receiver member.
Figure 6A:
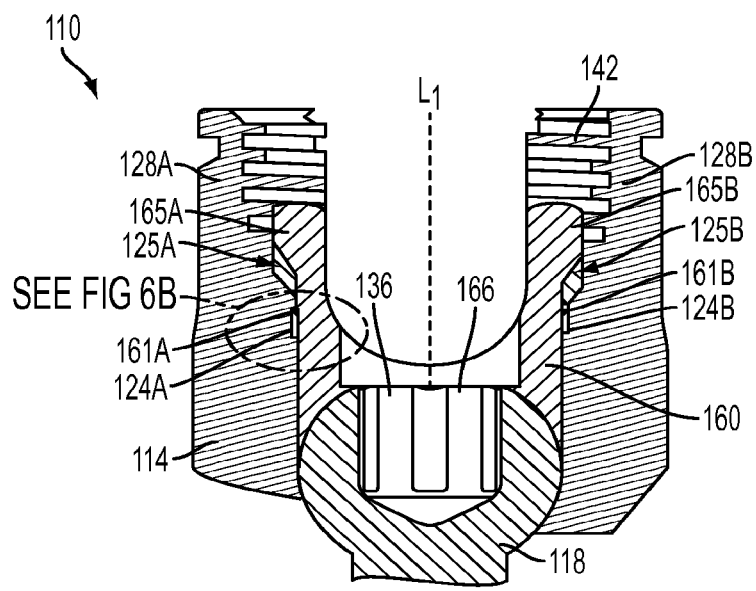
FIG. 6A is a partial cross-sectional view of the bone anchor assembly of FIG. 2 after the compression cap has been attached to the receiver member.
Figure 6B:
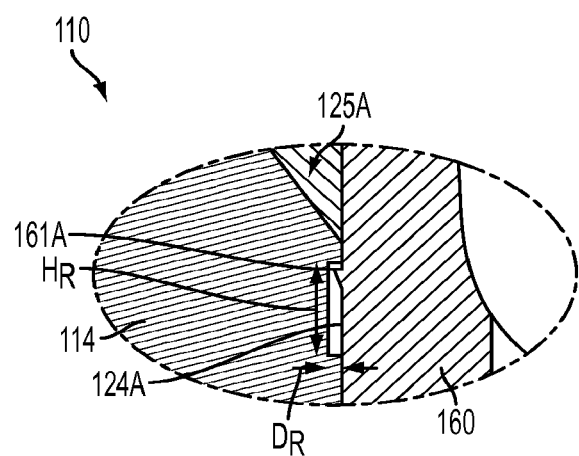
FIG. 6B is an enlarged cross-sectional view of the compression cap and the receiver member of the bone anchor assembly of FIG. 2 after the compression cap has been attached to the receiver member.
Figure 7:
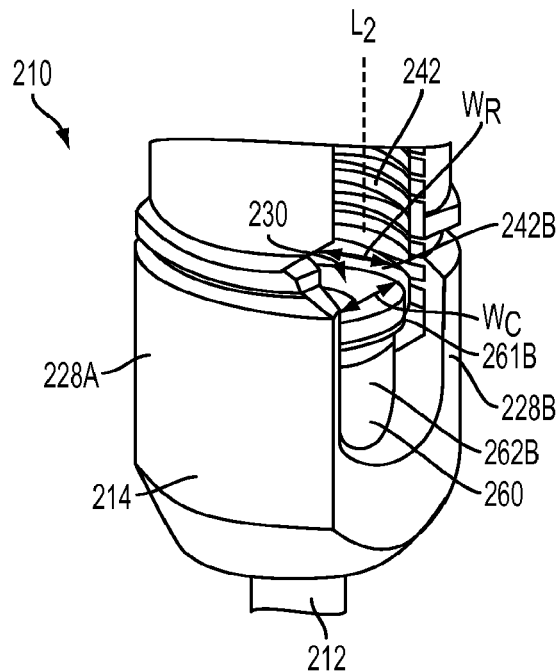
FIG. 7 is a partial perspective view of another embodiment of a bone anchor assembly having a bone anchor, a receiver member, and a compression cap, before the compression cap has been attached to the receiver member.
Figure 8:
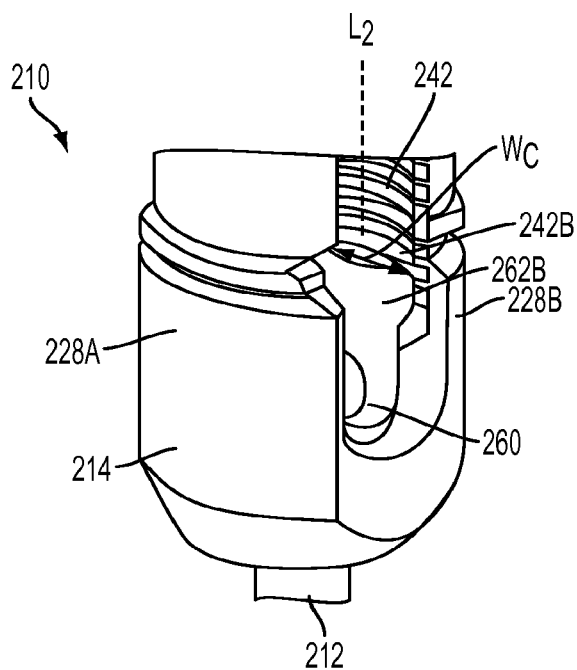
FIG. 8 is a partial perspective view of the bone anchor assembly of FIG. 7 after the compression cap has been attached to the receiver member.

In one embodiment, once the compression cap 160 is seated within the receiver member 114 in the secured configuration, with the wings 161A, 161B extending into the pockets 124A, 124B, a distal-facing surface 166 of the compression cap 160 can exert a frictional force on a proximal head 118 of the bone anchor 112 to substantially maintain the head 118 in a fixed position relative to the receiver member 114. The force should be sufficient to prevent free movement of the bone anchor 112 relative to the receiver member 114 while still allowing a user to move the receiver member 114 relative to the bone anchor 112. The force can vary slightly when the compression cap 160 is in the secured configuration, as the compression cap 160 can be capable of some longitudinal movement. As explained above, the pockets 124A, 124B can have a slightly greater height $H_R$ than a corresponding height He of the wings 161A, 161B, thereby allowing for slight movement of the wings 161A, 161B and thus the compression cap 160 along a longitudinal axis $L_1$ of the compression cap 160. This can be necessary to allow for minor adjustments to the angle of the bone anchor 112 and for further tightening of the compression cap 160 against the proximal head 118. As shown in FIGS. 5A and 6A, the proximal head 118 of the bone anchor 112 can be substantially spherical to match a corresponding spherical distal surface 166 of the compression cap 160, thus allowing for articulation of the bone anchor 112 at an angle to the longitudinal axis $L_1$ of the cap 160. When the compression cap 160 is distally advanced and in a locked configuration, e.g., by applying a closure mechanism (not shown) to the receiver member 114, the spherical distal surface 166 of the compression cap 160 can engage the proximal head 118 of the bone anchor 112 to thereby lock the bone anchor at a fixed position relative to the receiver member 114. While not shown, in certain embodiments the distal spherical surface 166 of the compression cap 160 and the proximal head 118 of the bone anchor 112 can each include opposed flats formed thereon and configured to limit angular movement of the bone anchor 112 to a single plane of motion, e.g., to thereby provide uniplanar motion.

The corresponding engagement features of a compression member and a receiver member can be of any shape and size, and can be configured to engage each other in a variety of ways. For example, an additional embodiment of a bone anchor assembly 210 having corresponding engagement features formed on a compression member and a receiver member is illustrated in FIGS. 7-11. The bone anchor assembly 210, as well as other bone anchor assemblies described herein, can generally be configured and used similar to the bone anchor assembly 110 of FIGS. 2-6. Additionally, like-named elements and like-illustrated elements of the bone anchor assembly 110 and of the other bone anchor assemblies discussed herein can be configured and used similar to one another.

FIGS. 7-11 illustrate the bone anchor assembly 210 having a compression cap 260 configured to secure a bone anchor 212 at a fixed angle to a receiver member 214. Corresponding engagement features formed on the compression cap 260 and the receiver member 214 can be configured to engage one another upon rotation of the compression cap 260 with respect to the receiver member 214. Thus, rotation of the compression cap 260 can move the compression cap 260 from an unsecured configuration, shown in FIG. 7, where the corresponding engagement features are unengaged, to a secured configuration, shown in FIG. 8, where the corresponding engagement features are engaged. In particular, a user can distally advance the compression cap 260 into a recess 230 of the receiver member 214 such that opposed arms 262A, 262B of the compression cap 260 are offset from opposed arms 228A, 228B of the receiver member 214, and then rotate the compression cap 260 while applying a distal force to cause the opposed arms 262A, 262B of the compression cap 260 to be aligned with the opposed arms 228A, 228B. In the illustrated embodiment, the angle of rotation required to move the compression cap 260 between the unsecured and the secured configurations is approximately 90 degrees, although the angle of rotation can vary from about 10 to 90 degrees depending on various factors, e.g., the dimensions of the opposed arms 262A, 272B of the compression cap 260 relative to the opposed arms 228A, 228B of the receiver member 214, the dimensions and location of the corresponding engagement features, etc.

Figure 9:
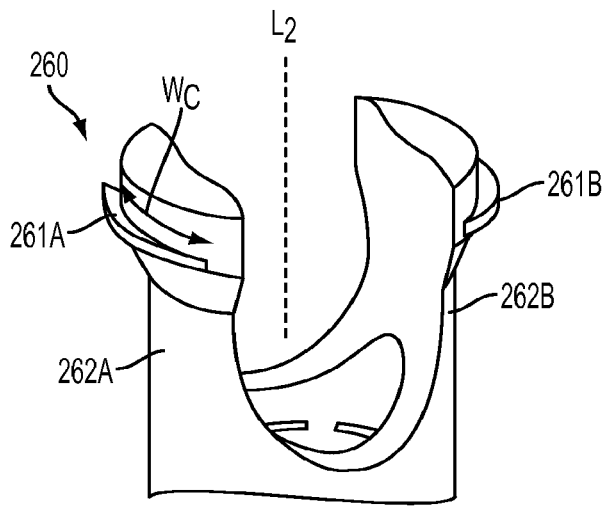
FIG. 9 is a perspective view of the compression cap of the bone anchor assembly of FIG. 7.

Engagement features of the compression cap 260 can be a variety of shapes and sizes, although in the illustrated embodiment the engagement features are in the form of wings 261A, 261B extending radially from the opposed arms 262A, 262B of the compression cap 260 and configured to engage complementary engagement features of the receiver member 214. As best seen in FIG. 9, both proximal and distal-facing surfaces of the wings 261A, 261B on the compression cap 260 are upwardly sloped at substantially the same angle to a longitudinal axis $L_2$ of the compression cap 260, such that radially outermost edges of the wings 261A, 261B are proximal of radially innermost edges of the wings 261A, 261B. The sloped surfaces of the wings 261A, 261B can thus allow distal advancement of the compression cap 260 into the receiver member, while substantially preventing proximal movement of the compression cap 260 and reducing a likelihood of loss or removal of the compression cap 260 once it is in the secured configuration. The compression cap 260 can be adjusted longitudinally while in the secured configuration, however, to allow for additional tightening of the compression cap 260 against the bone anchor 212 and/or for articulation of the bone anchor 212 to a desired angle, as discussed above.

Figure 10:
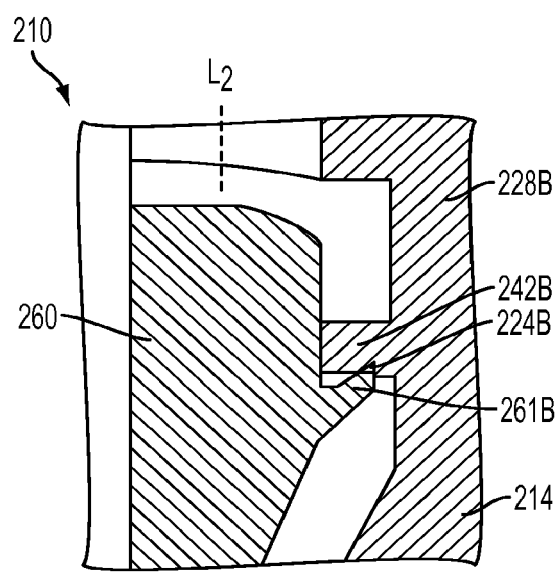
FIG. 10 is a partial cross-sectional view of the bone anchor assembly of FIG. 7.
Figure 11:
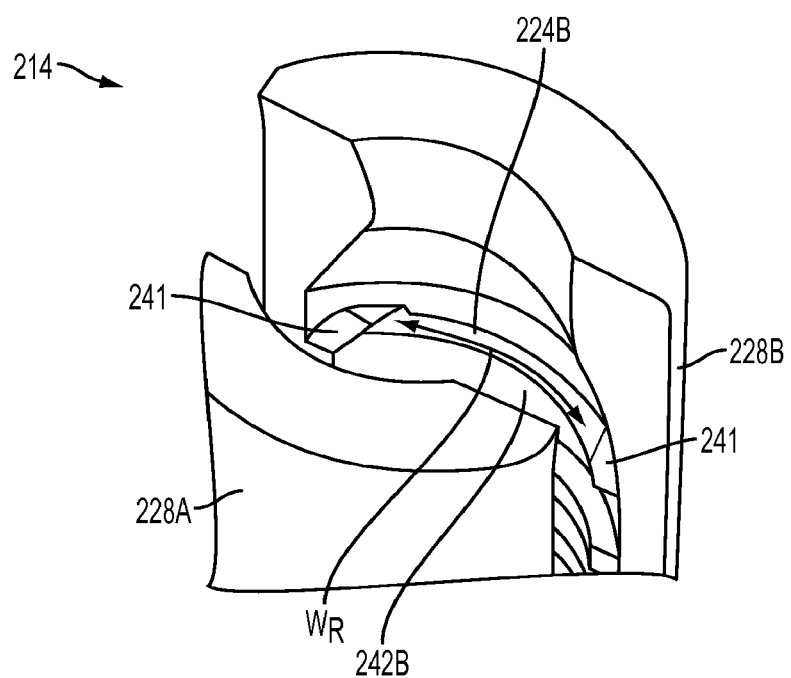
FIG. 11 is a partial cross-sectional perspective view of the receiver member of the bone anchor assembly of FIG. 7.

In this embodiment, shelves 242A, 242B extend radially inward from inner walls of the arms 228A, 228B of the receiver member 214 and are configured to engage the wings 261A, 261B of the compression cap 260. The shelves 242A, 242B can be disposed anywhere along the inner walls of the arms 228A, 228B, although in the illustrated embodiment the shelves 242A, 242B are disposed distally of threads 242 that can be configured to engage a closure mechanism, e.g., a set screw. As shown in FIG. 10, cut-outs 224A, 224B formed on distal-facing sides of the shelves 242A, 242B can be provided for receiving the wings 261A, 261B when the compression cap 260 is in the secured configuration, although it will be appreciated by a person skilled in the art that the shelves 242A, 242B do not require any modifications to engage the wings 261A, 261B. In another embodiment (not shown), any one or more of the threads 242 can be configured to engage the wings 261A, 261B.

Where provided, the cut-outs 224A, 224B of the receiver member 214 can be configured to facilitate transition of the compression cap 260 into the secured configuration, but to inhibit or prevent transition of the compression cap 260 out of the secured configuration. In the illustrated embodiment, shown in FIG. 11, the cut-outs 224A, 224B can have substantially the same dimensions as the wings 261A, 261B, although the cut-outs 224A, 224B can have at least one dimension that is slightly smaller than a corresponding dimension of the wings 261A, 261B to create an interference fit between the wings 261A, 261B and the cut-outs 224A, 224B and/or to allow for a snapping effect as the wings 261A, 261B are inserted into the cut-outs 224A, 224B. By way of non-limiting example, a width We of the wings 261A, 261B measured around a circumference of the compression cap 260 can be slightly larger than a width $W_R$ of the cut-outs 224A, 224B measured around a circumference of the receiver member 214, bounded on either end by ramped edges 241. The ramped edges 241 can have a slope inclined upwards towards a center of each of the cut-outs 224A, 224B, and planar side surfaces that abut opposite ends of the wings 261A, 261B when the compression cap 260 is in the secured position. The ramped edges 241 can thus provide a lead-in surface geometry as the wings 261A, 261B are rotated into the secured configuration and/or can inhibit removal of the compression cap 260 from the receiver member 214 by rotation once the compression cap 260 is in the secured configuration.

As with the previous embodiment, the wings 261A, 261B can be formed from a flexible material that is capable of being distally deflected as a user rotates the compression cap 260 from the unsecured to the secured configuration, such that the wings 261A, 261B are slightly bent by the ramped edges 241 as the compression cap 260 is rotated into the secured configuration and/or such that the wings 261A, 261B snap into alignment with the cut-outs 224A, 224B. In another embodiment, not shown, the wings 261A, 261B remain distally deflected while in the secured configuration, thus further securing the compression cap 260 to the receiver member 214 and providing additional distal force against the bone anchor 212.

Although the illustrated embodiments of bone anchor assemblies include male engagement features on a compression cap and female engagement features on a corresponding receiver member, the engagement features can be reversed with the compression cap having female engagement features and the receiver member having corresponding male engagement features. By way of non-limiting example, the receiver member can have wings extending from inner walls thereof that can be configured to engage recesses formed on outer surfaces of the compression cap. The wings and corresponding recesses can be configured and used similarly to those described above for bone anchor assemblies 110, 210.

In use, a bone anchor assembly can be assembled, either during manufacturing or intraoperatively, by passing an elongate shank of a bone anchor in a proximal-to-distal direction through an aperture formed in a distal end of a receiver member. A proximal head portion of the bone anchor can be polyaxially seated in a spherical recess formed in a distal portion of the receiver member. A compression member can be inserted between the opposed arms of the receiver member, proximal to the proximal head of the bone anchor. Corresponding engagement features of the compression member and the receiver member can be engaged by urging the compression member distally within the receiver member, or, in another aspect, by rotating and distally advancing the compression member into the receiver member. Engagement of the corresponding engagement features in a secured configuration can prevent proximal movement of the compression member with respect to the receiver member, thus securing the compression member within the receiver member. Such engagement can also cause the compression member to apply a frictional force to the head of the bone anchor to maintain the bone anchor at a fixed angle with respect to the receiver member. An angle of the bone anchor with respect to the receiver member can be adjusted by applying a force sufficient to overcome the frictional force.

The assembled bone anchor can be implanted in a bone of a patient. The bone can be prepared to receive the bone anchor assembly, e.g., by drilling an appropriately sized hole. A driver tool can be fitted with the bone anchor to drive the bone anchor into the prepared hole in the bone. A spinal fixation element, e.g., a rod, can be located in between the arms of the receiver member. A closure mechanism can be engaged with an inner thread formed on opposed arms of the receiver member, proximally of the rod, which can urge the compression member further distally to exert a frictional force on the head of the bone anchor and thus lock the bone anchor at a fixed angle with respect to the receiver member.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A method of assembling a bone screw, comprising:
   passing a shank portion of the bone screw through an aperture formed in a distal end of a receiver member such that a head portion of the screw is seated in the receiver member; and
   inserting a compression cap into the receiver member and engaging opposed projections extending radially outward from the compression cap with complementary recesses formed in the receiver member to retain the compression cap within the receiver member,
   wherein inserting the compression cap comprises rotating the compression cap relative to the receiver member to move the opposed projections into engagement with the complementary recesses, and
   wherein the complementary recesses are formed in a shelf that extends radially inward from an interior sidewall of the receiver member and said engaging comprises camming the opposed projections over ramped edges of the shelf and snapping the opposed projections into the complementary recesses.

2. The method of claim 1, wherein said engaging is effective to maintain the compression cap in a substantially fixed longitudinal position relative to the receiver member.

3. The method of claim 1, wherein said engaging is effective to maintain the compression cap in a substantially fixed rotational position relative to the receiver member.

4. The method of claim 1 wherein inserting the compression cap into the receiver member and engaging the opposed projections with the complementary recesses includes:
   deflecting free ends of first and second arms of the compression cap inwards during assembly of the compression cap to the receiver member and then deflecting the free ends of the first and second arms outward when the compression cap is seated in the receiver member; and
   engaging a ramped surface of the interior of the receiver member with ramped outer surfaces of the first and second arms of the compression cap.

5. A surgical method, comprising:
   passing an elongate shank of a bone anchor in a proximal-to-distal direction through an aperture formed in a distal end of a receiver member such that a proximal head portion of the bone anchor is polyaxially seated in a spherical recess formed in a distal portion of the receiver member;
   inserting a compression member between opposed arms of the receiver member proximal to the proximal head of the bone anchor such that opposed projections on an outer surface of the compression member engage with complementary recesses on an inner surface of the receiver member to prevent proximal movement of the compression member relative to the receiver member; and
   wherein inserting the compression member comprises rotating the compression member relative to the receiver member to move the opposed projections into engagement with the complementary recesses, and
   wherein the complementary recesses are formed in a shelf that extends radially inward from an interior sidewall of the receiver member and said rotating comprises camming the opposed projections over ramped edges of the shelf and snapping the opposed projections into the complementary recesses.

6. The method of claim 5, wherein the opposed projections of the compression member and the receiver member are positioned such that, when inserted, the compression member applies a frictional force to the head of the bone anchor to maintain the bone anchor at a fixed angle with respect to the receiver member.

7. The method of claim 6, further comprising applying a force sufficient to overcome the frictional force to adjust an angle of the bone anchor with respect to the receiver member.

8. The method of claim 5, further comprising:
   drilling an appropriately sized hole in a patient's bone; and
   driving the bone anchor into the prepared hole using a driver tool.

9. The method of claim 5, further comprising locating a spinal fixation element between the opposed arms of the receiver member proximal to the compression member.

10. The method of claim 9, further comprising engaging a closure mechanism with an inner thread formed on the opposed arms of the receiver member proximal to the spinal fixation element to urge the compression member further distally to exert additional frictional force on the head of the bone anchor and lock the bone anchor at a fixed angle relative to the receiver member.

11. The method of claim 5, wherein the complementary recesses features are effective to maintain the compression member in a substantially fixed longitudinal position relative to the receiver member.

12. The method of claim 5, wherein the complementary recesses features are effective to maintain the compression member in a substantially fixed rotational position relative to the receiver member.

13. The method of claim 5, wherein inserting the compression member includes:
   deflecting free ends of first and second arms of the compression member inwards and then deflecting the free ends of the first and second arms outward to engage the engagement features of the compression member with the corresponding features of the receiver member; and engaging a ramped surface of the interior of the receiver member with ramped outer surfaces of the first and second arms of the compression member.

\* \* \* \* \*